United States Patent
Yamagata et al.

(10) Patent No.: US 7,202,355 B2
(45) Date of Patent: Apr. 10, 2007

(54) DNA SEQUENCE REGULATING PLANT FRUIT-SPECIFIC EXPRESSION

(75) Inventors: Hiroshi Yamagata, Kobe (JP); Yasuo Aizono, Kobe (JP); Ayako Hirata, Higashiosaka (JP)

(73) Assignee: Kaneka Corporation, Osaka-shi (JP)

( * ) Notice: Subject to any disclaimer, the term of this patent is extended or adjusted under 35 U.S.C. 154(b) by 338 days.

(21) Appl. No.: 10/296,910

(22) PCT Filed: Dec. 1, 2000

(86) PCT No.: PCT/JP00/08505

§ 371 (c)(1),
(2), (4) Date: Mar. 24, 2003

(87) PCT Pub. No.: WO01/94575

PCT Pub. Date: Dec. 13, 2001

(65) Prior Publication Data

US 2004/0055039 A1    Mar. 18, 2004

(30) Foreign Application Priority Data

Jun. 2, 2000    (JP) .............................. 2000-165664

(51) Int. Cl.
*C07H 21/04* (2006.01)
*C12N 15/82* (2006.01)
*C12N 15/63* (2006.01)
*A01H 5/00* (2006.01)

(52) U.S. Cl. ............... 536/24.1; 435/252.3; 435/320.1; 435/419; 800/298

(58) Field of Classification Search ............... 536/24.1; 435/320.1, 419, 252.1, 41; 800/298
See application file for complete search history.

(56) References Cited

FOREIGN PATENT DOCUMENTS

| WO | WO 97/27308 A1 | 7/1997 |
|---|---|---|
| WO | WO 00/56863 A1 | 9/2000 |

OTHER PUBLICATIONS

Montgomery J. et al. Identification of an ethylene-responsive region in the promoter of a fruit ripening gene. Proc Natl Acad Sci U S A. Jul. 1, 1993;90(13):5939-43.*
Maiti I.B. et al. Promoter/leader deletion analysis and plant expression vectors with the figwort mosaic virus (FMV) full length transcript (FLt) promoter containing single or double enhancer domains. Transgenic Res. Mar. 1997;6(2):143-56.*
Doelling J.H. et al. The minimal ribosomal RNA gene promoter of *Arabidopsis thaliana* includes a critical element at the transcription initiation site. Plant J. Nov. 1995;8(5):683-92.*
Fiedler U. et al. A complex ensemble of cis-regulatory elements controls the expression of a *Vicia faba* non-storage seed protein gene. Plant Mol Biol. Jul. 1993;22(4):669-79.*
Yamagata et al., "Cucumisin, a Serine Protease from Melon Fruits, Shares Structural Homology with Subtilisin and Is Generated from a Large Precursor," *J. Biol. Chem.* (1994), vol. 269, No. 52, pp. 32725-32731.
Lasserre et al., "Differential activation of two ACC oxidase gene promoters from melon during plant development and in response to pathogen attack," *Mol. Gen. Genet.* (1997), vol. 256, No. 3, pp. 211-222.

* cited by examiner

*Primary Examiner*—Cynthia Collins
(74) *Attorney, Agent, or Firm*—Foley & Lardner LLP

(57) ABSTRACT

The present invention has for its object to provide a DNA sequence capable of regulating the expression of a desired gene specifically in the fruit of a plant, a plasmid containing that DNA sequence as well as a plant cell, plant body and microorganism transformed with the plasmid.

One aspect of the present invention is constituted by a fruit-specific expression-regulating unit DNA sequence which comprises a region comprising the base sequence shown under SEQ ID NO:1.

30 Claims, 2 Drawing Sheets

FIG. 1
pM1-B2-5 (4.2kb)
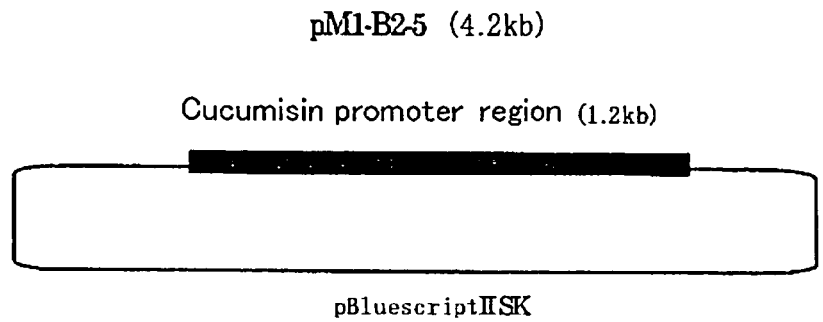
FIG. 2
pSKGUS3C (5.2kb)
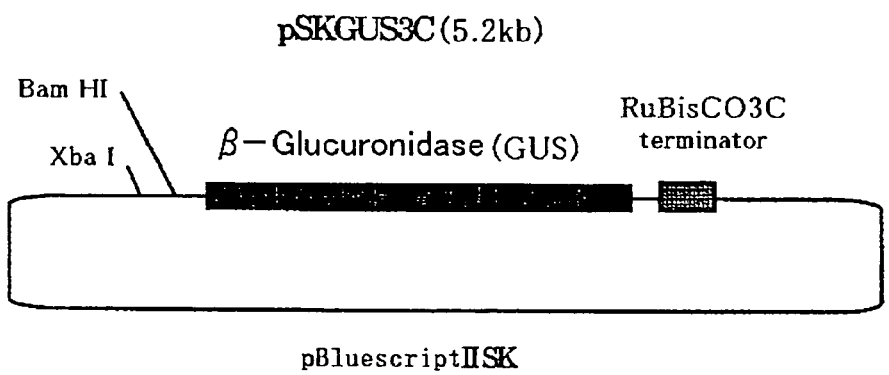
FIG. 3
| | Cucumisin promoter region | Plasmid name |
|---|---|---|
| −1181 | ——————————————— | p1181 |
| −865 | ——————————— | p865 |
| −371 | ———————— | p371 |
| −310 | ——————— | p310 |
| −254 | ————— | p254 |
| −234 | ———— | p234 |
| −214 | ——— | p214 |
| −200 | —— | p200 |
| −89 | — | p89 |

Derived from Cucumisin promoter    CaMV 35S Promoter

CaMV 35S Promoter pBI221 (5.6kb)

pUC19 p35S-INT-LUC+ (5.5kb)

pUC19

SEQUENCE LISTING

<160> NUMBER OF SEQ ID NOS: 8

<210> SEQ ID NO 1
<211> LENGTH: 20
<212> TYPE: DNA
<213> ORGANISM: Cucumis melo
<220> FEATURE:
<223> OTHER INFORMATION: L. var. reticulatus cv. Teresa

<400> SEQUENCE: 1
gacacgtgtc acaacctaat                                                     20

<210> SEQ ID NO 2
<211> LENGTH: 56
<212> TYPE: DNA
<213> ORGANISM: Cucumis melo
<220> FEATURE:
<223> OTHER INFORMATION: L. var. reticulatus cv. Teresa

<400> SEQUENCE: 2
tgagcttctc ttagtgtact atatccttta atattaatgc atctttcgat cttgct            56

<210> SEQ ID NO 3
<211> LENGTH: 1181
<212> TYPE: DNA
<213> ORGANISM: Cucumis melo
<220> FEATURE:
<223> OTHER INFORMATION: L. var. reticulatus cv. Teresa

<400> SEQUENCE: 3
gatcttactt taccataatg gtgaaaagga tagagaccca catggttttt acttcgttat          60
agagacaaga tgaaaacaaa tctaaaattt aatattatag atggatagat gatggacaac         120
aaaagagaa aagaagatac tggtcattgg tccaaaacag ccacccgaat caatatatga         180
ccgaaaaaca aaagctacag aatcatatct gtgcaacggt gccacagtgc tataggatag         240
cacaaccaca ctgtcacata aaaagagga ttttgcactc gttttagatg gagtttcgta         300
attttcgggt ctttcaagct taaatatata cttcattaaa gcttcgaatt ttgtaatgtt         360
caattctacc tctttgatgt tcgatacccta taaataatt aaataaacgt atagacgtag         420
gaacaattaa gcggagttag atagtgcatt tatgattcta cctgtgagtg caatggtaaa         480
atggacatta taaagagta ggggcaaaga gggaagtgaa aaattctccc cacttagcca         540
tgtttaatat agtagggata ggaatatgta ataagtagtg tttttttctat ttaattttct        600
gtatacttct tccatctcct ttaattatta aaaggttttc ctctctttac tctttctctc         660
taaattacta ttctgaagta tattttcttt tataaaaaga gtaataaact ttatttccat         720
taaaagaaca aacaacaaga aatgataatc aaatacacat tcatattttt aaaaaaaaag         780
ttaaacaaga tatagaaata gttatcaaat atatttatgt tgtcattcct tgtatacaat         840
ggcattcctt tagctttgtt tatgtatttc ctgagcttct cttagtgtac tatatccttt         900
aatattaatg catctttcga tcttgctaag atatgataaa aatagacgac acgtgtcaca         960
acctaattga gatatttcga tgtactttct atccgtctta gcttgtaatt aattattgtt         1020
aaaaagaat actcaattaa ctagaaacaa gaaataagaa acgaaaacat tacaaaacgg         1080
agttgaagcg tgcaaatttg tggaaatgat tgttatcatg aaccagaaaa cattaaataa         1140
ctcttcctat aaaaggcccct tattcttcac tttctcaaat c                            1181

<210> SEQ ID NO 4
<211> LENGTH: 30
<212> TYPE: DNA
<213> ORGANISM: Cucumis melo
<220> FEATURE:
<223> OTHER INFORMATION: L. var. reticulatus cv. Teresa

<400> SEQUENCE: 4
agaagacata gtagtgcttt ttgctatcag                                          30

```
<210> SEQ ID NO 5
<211> LENGTH: 21
<212> TYPE: DNA
<213> ORGANISM: Cucumis melo
<220> FEATURE:
<223> OTHER INFORMATION: L. var. reticulatus cv. Teresa

<400> SEQUENCE: 5
tgtatacatg gggaggaagc t                                               21

<210> SEQ ID NO 6
<211> LENGTH: 31
<212> TYPE: DNA
<213> ORGANISM: Cucumis melo
<220> FEATURE:
<223> OTHER INFORMATION: L. var. reticulatus cv. Teresa

<400> SEQUENCE: 6
tagaagcgag tcgattactg aagaaaagac t                                    31

<210> SEQ ID NO 7
<211> LENGTH: 40
<212> TYPE: DNA
<213> ORGANISM: Cucumis melo
<220> FEATURE:
<223> OTHER INFORMATION: L. var. reticulatus cv. Teresa

<400> SEQUENCE: 7
aagatatgat aaaaatagac gacacgtgtc acaacctaat                           40

<210> SEQ ID NO 8
<211> LENGTH: 39
<212> TYPE: DNA
<213> ORGANISM: Cucumis melo
<220> FEATURE:
<223> OTHER INFORMATION: L. var. reticulatus cv. Teresa

<400> SEQUENCE: 8
acctaattga gatatttcga tgtactttct atccgtctt                            39
```

DNA SEQUENCE REGULATING PLANT FRUIT-SPECIFIC EXPRESSION

TECHNICAL FIELD

The present invention relates to a DNA sequence for gene expression and regulation in plant fruits and the use thereof. More particularly, it relates to a DNA sequence for specifically regulating gene expression in plant fruits, a plasmid containing that DNA sequence, a plant cell, plant body and microorganism transformed with that plasmid.

BACKGROUND OF THE INVENTION

A technique is known for creating a transgenic plant transformed with DNA sequences comprising a gene coding for a desired protein capable of being expressed in a plant and a certain promoter sequence in order to express that protein. One of such promoters is the cauliflower mosaic virus (CaMV) 35S promoter capable of allowing non-tissue-specific expression of a desired protein in a plant. As regards protein expression systems in plants, inducible gene promoters capable of reacting with an exogenous chemical substance have also been reported, for example a system in which the tetracycline-inducible Tn10 Tet repressor is utilized (The Plant J. (2), 397, 1992) and a system in which the steroid hormone-inducible rat glucocorticoid receptor is utilized (The Plant J. (11), 605, 1997). As regards base sequences involved in tissue-specific expression of plant genes, the so-called RY core sequence CATGCAT associated with a gene that is expressed in a seed-specific manner is known (Plant Physiol. (98), 387, 1992). It has also been disclosed that a desired protein can be expressed in raspberry fruit by using the raspberry drul promoter (Japanese Kohyo Publication 2000-503848).

Cucumisin, a plant-derived protease, is a thermostable alkaline serine protease which is abundantly accumulated in melon juice (Agric. Biol. Chem. (53), 1009, 1989) and cDNA therefor has been cloned (J. Biol. Chem. (52), 32725, 1994)). However, the regulating mechanisms of its fruit-specific expression remain unknown.

Transgenic crop plants transformed with a herbicide resistance gene or the like by utilizing the technology of introducing a heterologous DNA into plants to create transgenic plants have already been utilized in food production. On the other hand, another method of utilizing transgenic plants, namely the development into the so-called molecular agriculture in which plants are caused to produce useful proteins and the products are extracted for utilization, cannot yet be said to have been established as an industry. When plant cells are or a plant body is caused to produce a useful protein or a useful substance resulting from conversion thereof, there arise the possibility that if the product is expressed in the leaf, stem or root, the extraction efficiency or purification/recovery of the product may become or encounter problems in some not only in the case of non-tissue-specific expression in a plant but also in the case of specific expression. A promoter readily controllable and ensuring good production efficiency is thus desired. The fruit is a storage organ by far greater in volume than seeds and, in particular, the gourd family, typically melon, is characterized by its producing a great number of relatively large fruits. If a technology of accumulating a useful protein or useful substance in those fruits or giving them desired properties is established, the technology will become a very useful one. While there are several reports about the base sequences involved in expression specific to the seed, leaf or root of plants, there is no report found about the identification and utilization of a base sequence, in particular a melon promoter sequence, involved in fruit-specific expression.

SUMMARY OF THE INVENTION

In view of the above-discussed state of the art, the present invention has for its object to provide a DNA sequence capable of regulating the expression of a desired gene specifically in the fruit of a plant, a plasmid containing that DNA sequence as well as a plant cell, plant body and microorganism transformed with the plasmid.

As a result of intensive investigations, the present inventors could identify a novel regulatory DNA sequence involved in fruit-specific expression in a region upstream of the melon-derived cucumisin gene coding for a protein expressed at a high level specifically in the fruit and found that the DNA sequence functions in site-specific expression in the plant body. Based these findings, they have completed the present invention.

Thus, in a first aspect, the present invention consists in a fruit-specific expression regulating unit DNA sequence which comprises a region comprising the base sequence shown under SEQ ID NO:1, SEQ ID NO:2, SEQ ID NO:3 or SEQ ID NO:7. The DNA sequence according to the first aspect of the present invention can be preferably regulated by a transcription factor capable of binding to the base sequence shown under SEQ ID NO:1, SEQ ID NO:2, SEQ ID NO:3 or SEQ ID NO:7 and involved in fruit-specific expression.

In a second aspect, the present invention relates to a plasmid which comprises a DNA coding for a structural gene capable of being expressed in a plant or for a corresponding antisense RNA, a promoter and a terminator capable of functioning in the plant, and the DNA sequence according to the first aspect of the invention.

In a third aspect, the present invention relates to a plant cell or a plant which is able to express a protein or a corresponding antisense RNA encoded by a desired structural gene in a fruit-specific manner with the plasmid according to the second aspect of the present.

In a fourth aspect, the present invention relates to a microorganism harboring the plasmid according to the second aspect of the present invention.

BRIEF DESCRIPTION OF THE DRAWINGS

FIG. 1 is a schematic representation of a plasmid, pM1-B2-5, containing a cucumisin promoter region as an insert DNA.

FIG. 2 is a schematic representation of a plasmid, pSKGU3C, for promoter activity measurement.

FIG. 3 is a schematic representation of the cucumisin promoter region DNA sequence in a plasmid, pSKGU3C, as inserted at the XbaI-BamHI site thereof, and of plasmids constructed therefrom.

DETAILED DISCLOSURE OF THE INVENTION

Figure 4:
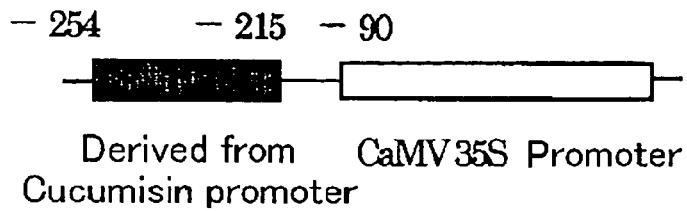
FIG. 4 is a schematic representation of the DNA sequence inserted into a plasmid, pSKGU3C, at the XbaI-BamHI site thereof in constructing a plasmid, pKGX.
Figure 5:
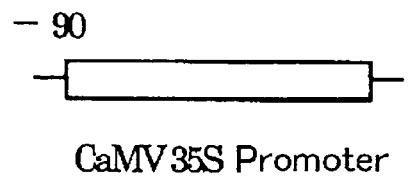
FIG. 5 is a schematic representation of the DNA sequence inserted into a plasmid, pSKGU3C, at the XbaI-BamHI site thereof in constructing a plasmid, pX.
Figure 6:
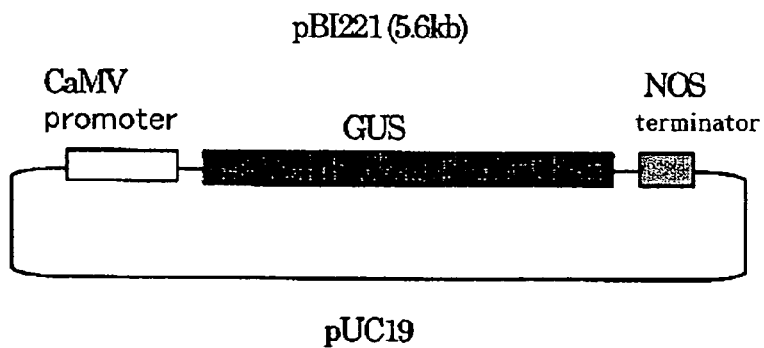
FIG. 6 is a schematic representation of a plasmid, pBI221.

In the following, the present invention is described in detail.

In a first aspect, the present invention is directed to a fruit-specific expression regulating DNA sequence capable of functioning in plant cells which is a DNA sequence being able to function as a fruit-specific expression regulating unit and comprises a region comprising the base sequence shown under SEQ ID NO:1, SEQ ID NO:2, SEQ ID NO:3 or SEQ ID NO:7.

The DNA sequence according to the first aspect of the invention may contain one of the sequences shown under SEQ ID NO:1, SEQ ID NO:2 and SEQ ID NO:7 singly or may contain two or more of them. As a specific region containing the sequence shown under SEQ ID NO:1 or SEQ ID NO:7 and/or the sequence shown under SEQ ID NO:2, there may be mentioned a region which is a melon gene and contains the base sequence shown under SEQ ID NO:3.

The DNA sequence according to the first aspect of the invention is a sequence containing a region derived from the cucumisin promoter gene of melon and can regulate the fruit-specific expression and, therefore, when the DNA sequence of the invention is used, a fruit can be provided with any desired property. For example, it is possible to produce a useful substance in a site-specific manner in fruits, which are promising storage organs in plants, or inhibit the transcription of a specific gene to be expressed in fruit.

The DNA sequence according to the first aspect of the invention is preferably regulated by a transcription factor involved in fruit-specific expression and capable of binding to the base sequence shown under SEQ ID NO:1, SEQ ID NO:2, SEQ ID NO:3 or SEQ ID NO:7.

The above-mentioned transcription factor includes, among others, a nucleoprotein binding to the DNA sequence shown under SEQ ID NO:7, a GATA box-binding protein, an I-box-binding protein, a G-box-binding protein, and a protein capable of binding to the Gb probe in gel shift assay as shown herein in Example 7.

For the DNA sequence according to the first aspect of the invention to function as a fruit-specific expression-regulating promoter, it is necessary that a transcription factor should bind to the above DNA sequence. Therefore, the expression of a desired useful substance, for instance, can be regulated by gene transfer of the transcription factor into cells.

In accordance with the first aspect of the invention, those base sequences derived from the respective base sequences by partial mutation, substitution, deletion or a like procedure that will not impair the functions of course fall within the scope of the present invention.

In accordance with the first aspect of the invention, it is also possible to make a protein encoded by a structural gene regulated by a promoter having activity in plants be expressed in a fruit-specific manner by linking, inserting or substituting a base sequence which contained in the sequence shown under SEQ ID NO:1, SEQ ID NO:2, SEQ ID NO:3 or SEQ ID NO:7 to, into or for a promoter capable of functioning in other plants, for example the cauliflower mosaic virus (CaMV) 35S promoter.

Although any of those so-far known definite plant hormone-responsive elements, such as the ethylene-responsive element and auxin-responsive element, cannot be found in the DNA sequence according to the first aspect of the invention, the sequence may function in cooperation with an unidentified plant hormone element or the like to cause the fruit-specific expression.

Further, as shown in Table 1 in Example 4, it is suggested that the DNA sequence shown as bases NO.1 to 20 in SEQ ID NO:7 might include a DNA sequence functioning as an expression inhibiting element. It is readily anticipated that a procedure, such as deletion or substitution, applied to the DNA sequence in that portion might exert an obvious influence on the fruit-specific expression.

In the practice of the invention according to the first aspect thereof, the fruit is not particularly restricted but widely includes fruits obtainable from seed plants. Advantageously used are, however, plants of the gourd family (Cucurbitaceae), such as melon, watermelon, gourd, cucumber and cushaw (pumpkin). Melon is preferred among others, since it is great in fruit size, hence can store a large amount of a useful substance.

The base sequences shown under SEQ ID NO:1, SEQ ID NO:2, SEQ ID NO:3 and SEQ ID NO:7 are derived from the melon cucumisin promoter sequence, and the DNA sequence according to the first aspect of the invention can be obtained in the conventional manner, for example, by extracting genomic DNA from melon and carrying out the IPCR using primers prepared based on the exon sequence of cucumisin.

A regulatory function of the DNA sequence according to the first aspect of the invention in a plant body or plant cells can be checked with a sufficient level of reliability by transient expression using the particle bombardment method for site-specific expression examination.

In accordance with the second aspect, the invention consists in a DNA coding for a structural gene capable of being expressed in plants or a corresponding antisense RNA as well as a plasmid having a promoter and a terminator capable of functioning in plants and the DNA sequence according to the first aspect of the invention.

The above structural gene and antisense RNA are not particularly restricted but can adequately be selected according to the intended purpose.

The above-mentioned promoter is not particularly restricted but may be any of those capable of functioning in plant cells. Thus, mention may be made, for example, of the cauliflower mosaic virus (CaMV) 35S promoter, the octopine synthesis gene promoter of *Agrobacterium*, the tobacco PR1a gene promoter, and the tomato ribulose 1,5-diphosphate carboxylase oxidase small subunit promoter.

The above-mentioned terminator is not particularly restricted but may be any of those capable of functioning in plant cells. Thus, there may be mentioned, for example, the RuBisCO 3C gene or plant gene-derived nopaline synthesis gene terminator, and the garlic virus GV1 or GV2 gene terminator.

The plasmid according to the second aspect of the invention can be constructed in the conventional manner using one of various known vectors.

When the plasmid is introduced into cells by the electroporation, particle bombardment, microinjection or fusion method, for instance, the above vector is not particularly restricted but use can be made of any of the known vectors, such as pBR322, pBR325, pUC19, pUC119, pBluescript, pBluescript SK and pBluescript II SK. When the plasmid transfer is to be realized by the method of infecting plant cells with *Agrobacterium*, mention may be made, for example, of such vectors as the binary vectors pBI101 (product of Clontech), pBI121 (product of Clontech) and pBI221 (product of Clontech).

The plasmid according to the second aspect of the invention can be obtained by inserting, into such a vector, the DNA sequence according to the first aspect of the invention, namely a DNA coding for a structural gene capable of being expressed in plants or a corresponding antisense RNA, and a promoter and a terminator capable of functioning in plants.

Furthermore, when a promoter having a fruit-specific expression regulating DNA sequence according to the first aspect of the invention is used to express of a protein, it is also possible to positively cause secretion a protein in a fruit or fruit juice or positively allowing the matter conversion reaction(s) involving such a protein or a plurality of such proteins to proceed in a plant fruit for the production of a useful substance resulting from such reaction(s) by linking, upstream of the protein-encoding gene capable of being expressed in plants, a signal sequence necessary for extracellular secretion of the protein, for example the secretory signal-encoding DNA sequence of the melon cucumisin gene or the secretory signal-encoding DNA sequence of some other gene or, downstream from the gene coding for said protein, a DNA sequence coding for a localization signal governing the localizability of the protein in cells.

Furthermore, it is also possible to cause expression of a corresponding antisense RNA of the gene coding for a protein involved in the overripe of fruit, in addition to the expression of the desired protein, for an improvement in storability or like controlling purposes.

For facilitating the transformant plant selection, a selective marker gene may be inserted into the plasmid according to the second aspect of the invention. The selective marker gene may be, for example, an antibiotic resistance gene, such as the G418, hygromycin, bleomycin, kanamycin, gentamicin, chloramphenicol resistance gene or the like. When the plasmid contains an antibiotic resistance gene, a transgenic plant, namely a plant transformed with the plasmid of the invention introduced therein, can be selected with ease by selecting a plant capable of growing in a medium containing the antibiotic.

By transforming a plant cell or a plant body using the plasmid according to the second aspect of the invention, it becomes possible to specifically produce a desired useful substance, or inhibit the production of an unnecessary substance, in the fruit of that plant.

As the method of introducing the DNA sequence according to the first aspect of the invention or the plasmid according to the second aspect of the invention into a plant cell or a plant body for the purpose of fruit-specific expression, there may be such known methods as the technique of plant cell infection with *Agrobacterium*, the electroporation method, the particle gun method, the microinjection method, and the technique comprising fusion of protoplast with a vector-containing small cell, cell or lysosome, for instance.

In accordance with the third aspect, the invention provides a plant cell or plant body capable of fruit-specifically expressing the protein or antisense RNA encoded by the target structural gene owing to the occurrence of the plasmid according to the second aspect of the invention.

The above plant cell or plant body is not particularly restricted but may be any of those capable of producing fruit. Preferred are, however, plants of the gourd family, such as melon, watermelon, gourd, cucumber and cushaw.

In accordance with the fourth aspect, the invention provides a microorganism harboring the plasmid according to the second aspect of the invention.

As the above microorganism, there may be mentioned, among others, *Agrobacterium* species and *Escherichia coli*.

It is also possible to produce the plant cell or plant body according to the third aspect of the invention using an *Agrobacterium* strain harboring the plasmid according to the second aspect of the invention.

When a plant is infected with such an *Agrobacterium* strain, part of the plasmid DNA harbored in the bacterial cells is transferred to the plant genome. Thus, by utilizing this characteristic, it is possible to introduce, into plants, the DNA according to the first aspect of the invention or the DNA coding for a structural gene capable of being expressed in plants or a corresponding antisense RNA, together with a promoter and a terminator capable of functioning in plants.

In cases where the plasmid according to the second aspect of the invention has no vir region, the *Agrobacterium* strain to be used is required to have another plasmid containing the vir region.

BEST MODES FOR CARRYING OUT THE INVENTION

The following examples illustrate the present invention in further detail. They are, however, by no means limitative of the scope of the present invention.

EXAMPLE 1

Isolation of the Cucumisin Protein Promoter from Melon Genomic DNA (1) Preparation of Melon Genomic DNA Leaves (10 g) of a seedling of muskmelon (*Cucumis melo L. reticulatus* cv. *Teresa*) were cut to pieces and ground in liquid nitrogen. The ground matter was suspended in 2×CTAB buffer (2% CTAB, 1.4 M NaCl, 100 mM Tris-HCl (pH 8.0), 20 mM EDTA, 1% polyvinylpyrrolidone) and, after 10 minutes of heating at 55° C., chloroform-isoamyl alcohol (24:1) was added, and the mixture was gently mixed up by inverting at room temperature for 30 minutes. After 15 minutes of centrifugation at 14000×g, chloroform-isoamyl alcohol (24:1) was added to the upper layer, and 1×CTAB buffer to the intermediate layer and bottom layer, followed by gentle mixing up by inverting and centrifugation. The upper layers were combined, and a 1/10 volume of 10% CTAB solution (10% CTAB, 0.7 M NaCl) was added, followed by mixing up by inverting. Further, an equal volume of CTAB precipitation buffer (1% CTAB, 50 mM Tris-HCl (pH 8.0), 10 mM EDTA) was added, followed by gentle mixing up by inverting and centrifugation. 1 M NaCl-TE buffer (1 M NaCl, 10 mM Tris-HCl (pH 8.0), 1 mM EDTA) was added to the precipitate obtained for dissolution of the precipitate. Thereto was added an equal volume of isopropanol and, after gentle mixing up by inverting, the mixture was centrifuged. The precipitate obtained was washed with 70% ethanol and dried and dissolved in TE buffer. After dissolution, RNase A and proteinase K were added to the respective final concentrations of 5 μg/ml and 10 μg/ml and, after 30 minutes of heating at 50° C., the mixture was extracted with phenol-chloroform-isoamyl alcohol (25:24:1). A 1/10 volume of 3 M sodium acetate solution (pH 5.2) and an equal volume of isopropanol were added to the upper layer, the resulting mixture was centrifuged, and the precipitate was washed with 70% ethanol and dissolved in TE buffer to give a genomic DNA solution.

(2) Promoter Region Cloning by the IPCR (Inverse PCR)

The thus-prepared DNA solution containing 1 μg of melon genomic DNA was treated overnight with 10 units each of the restriction enzymes BamHI and BglII at 37° C. The digested DNA fragments were recovered by ethanol precipitation, and subjected to reaction using 10 units of T4

DNA ligase at 15° C. for 12 hours. To this DNA fraction were added 10 ng of cucumisin primer 1 (SEQ ID NO:4) and 10 ng of cucumisin primer 2 (SEQ ID NO:5), and a DNTP mixture (to each final dNTP concentration of 0.2 mM) and 0.5 µl of AmpliTaq Gold DNA Polymerase were added to give a 100-µl solution, and the PCR was carried out using a Zymoreactor (product of ATTO, type AB-1800); thus, after 10 minutes of treatment at 95° C., 30 cycles each comprising 1 minute at 94° C., 2 minutes at 55° C. and 3 minutes at 72° C. were repeated, followed by 7 minutes of final PCR treatment at 72° C. After completion of the reaction, the amplified DNA fragment was inserted into a plasmid fragment prepared by cleaving pBluescript II SK with the restriction enzyme SmaI and adding one base T to the 5' terminus thereof, to give a plasmid, pM1-B2-5 (FIG. 1). The DNA sequencing of the insert fragment was carried out using a DNA sequencer (model 4000L; product of LI-COR, Inc., NE, USA) and the SequiTherm EXCEL II Cycle Sequencing Kit-LC (product of Epicentre Technologies, Madison, Wis., USA). As a result, the base sequence of an about 1.2 kb cucumisin promoter site shown under SEQ ID NO:3 was determined.

EXAMPLE 2

When an expression analysis is carried out using the promoter sequence of an isolated gene, it is desirable to construct a fusion gene resulting from linking of a reporter gene enabling an easy activity assay at a site as close as possible to the transcription initiation point of the original gene. Therefore, the transcription initiation point of the isolated cucumisin gene was determined.

The Ex primer (SEQ ID NO:6) terminally labeled with [$\gamma$-$^{32}$P]ATP using T4 polynucleotide kinase was allowed overnight at 42° C. to hybridize with 20 µg of poly(A)+ RNA extracted from the core of an immature muskmelon fruit at 10 days after pollination. Using the reaction mixture, the primer extension reaction by reverse transcription was carried out by adding 12.5 units of AMV RT (product of LIFE SCIENCE, INC.) and incubating for 1 hour at 55° C. Subsequently, the ethanol precipitation product was subjected to polyacrylamide gel electrophoresis with a sequencing gel composition. As a result, only one transcription initiation point was found for the cucumisin gene (a: adenine following SEQ ID NO:3).

EXAMPLE 3

Construction of a Melon Promoter-GUS Fusion Gene

A vector for promoter activity assaying, pSKGUS3C, was constructed by joining, to the plasmid pBluescript II SK, the pBI221 vector (Clontech Laboratories, Inc.)-derived β-glucuronidase (GUS) gene, as a reporter gene, and the RuBisCO 3C gene, as a terminator (FIG. 2). Then, PCR was carried out using the pM1-B2-5 plasmid as the template, together with a primer having a restriction enzyme XbaI site as designed to successively delete the upstream portion of the cucumisin promoter sequence and a primer having a BamHI site as resulting from cleavage at a site one base upstream of the transcription initiation point. The thus-obtained DNA fragments differing in length were inserted between the restriction enzyme sites XbaI and BamHI occurring upstream of the GUS gene of pSKGUS3C to construct cucumisin promoter-GUS fusion genes. In indicating bases in a promoter region, the base immediately before the transcription initiation point is generally numbered −1. Thus, when the 3' terminus of the base sequence under SEQ ID NO:3 is numbered −1 and the 5' terminus −1181, there were specifically constructed the p1181 plasmid having the sequence −1181 to −1 of the cucumisin promoter, the p865 plasmid having the sequence −865 to −1, the p371 plasmid having the sequence −371 to −1, the p310 plasmid having the sequence −310 to −1, the p254 plasmid having the sequence −254 to −1, the p234 plasmid having the sequence −234 to −1, the p214 plasmid having the sequence −214 to −1, the p200 plasmid having the sequence −200 to −1, the p89 plasmid having the sequence −89 to −1, the pKGX plasmid resulting from joining the −90 to −1 region of the cauliflower mosaic virus (CaMV) 35S promoter to the downstream portion of the sequence −254 to −215, and the pX plasmid having the −90 to −1 region of the cauliflower mosaic virus (CaMV) 35S promoter. pBI221 having an about 800 bp portion of the cauliflower mosaic virus (CaMV) 35S promoter was used as a positive control (FIG. 3 to FIG. 6).

EXAMPLE 4

Site-Specific Expression of the Cucumisin Promoter (1) DNA Shooting into Organs by the Particle Bombardment An immature muskmelon fruit (about 4.5 cm in diameter) cut to pieces about 1 to 2 mm in thickness and leaves and the stem cut to an appropriate size were placed in plastic dishes having a diameter of 9 cm.

70% Ethanol (1 ml) was added to 60 mg of gold particles having a diameter of 1.6 µm, and the mixture was vortexed for 5 minutes, allowed to stand for 15 minutes and then centrifuged for 5 seconds, and the supernatant was removed. Further, the procedure comprising addition of 1 ml of sterilized water, 1 minute of vortexing, 1 minute of standing and 2 seconds of centrifugation was repeated 3 times and, then, 50% glycerol was added to make the final gold particle concentration 60 mg/ml.

While vigorously vortexing 50 µl of the gold particle preparation, 5 µl (containing about 1.2 pmole) of each solution of the p1181, p865, p371, p200, pSKGUS3C or pBI221 plasmid was added and, after further addition of 50 µl of a 2.5 M calcium chloride solution and 20 µl of a 0.1 M spermidine solution, the mixture was vigorously vortexed for 3 minutes. After 1 minute of standing and 2 seconds of centrifugation, the supernatant was removed and the pellet was resuspended in ethanol. The pellet was placed on the middle of a microcarrier and dried.

The gold particles with each fusion gene adsorbed thereon were shot twice into samples of the immature fruit, leaves and stem for each kind of DNA. For the shooting, the Biolistic PDS-1000/He particle Delivery System (product of Bio-Rad) was used.

(2) GUS Activity Staining in Organs

After completion of the shooting, the dishes were closely sealed and wrapped with an aluminum foil for shielding against light, and incubated at 25° C. for 24 hours. Each sample was further immersed in a GUS staining solution (50 mM sodium phosphate (pH 7.0), 10 mM EDTA, 0.5 mM potassium hexacyanoferrate(II), 0.5 mM potassium hexacyanoferrate(III), 1 mM X-Gluc, 2% DMSO, 0.1% Triton X-100), tightly sealed, incubated overnight in the dark at 37° C., then decolorized in ethanol, and checked, by staining, for the expression of the GUS protein in the immature melon fruit, mature leaf and stem by various cucumisin promoters. The results are shown in Table 1.

TABLE 1

| Plasmid | Fruit | Mature leaf | Stem |
|---|---|---|---|
| p1181 | +++ | − | − |
| p865 | +++ | − | − |
| p371 | +++ | − | − |
| p200 | − | +/− | +/− |
| pSKGUS3C | − | − | − |
| pBI221 | +++ | +++ | +++ |

+++: strong staining
+/−: very weak staining
−: no staining

EXAMPLE 5

Identification of a Fruit-Specific Expression Regulating DNA Region in the Cucumisin Promoter (1) Plasmids Used The method of DNA shooting into various organs by the particle bombardment was the same as in Example 4, and the structures of the plasmids used were as shown in Example 3.

(2) Preparation of Extracts

The immature melon fruit and mature leaf samples prepared by the method shown in Example 4 (1) were each ground in liquid nitrogen and, after thawing at room temperature, 1× PicaGene cultured cell lysing agent containing 2 mM DFP was added, followed by grinding and centrifugation. Each supernatant was used as an extract sample.

(3) GUS Activity Assay

Figure 7:
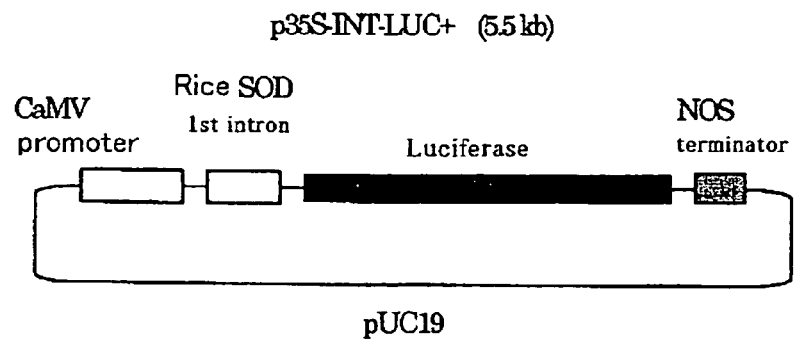
FIG. 7 is a schematic representation of a plasmid, p35S-INT-LUC+.

For determining the GUS activity, p35S-INT-LUC+(FIG. 7) produced by inserting, into the pUC19 vector, the cauliflower mosaic virus (CaMV) 35S promoter, INT (first intron of the rice SOD gene) and LUC (firefly luciferase gene) was shot simultaneously, and the luciferase activity thus assayed was used for GUS activity standardization.

For GUS activity assaying, 4-methylumbelliferyl-β-D-glucuronide was added to a final concentration of 1 mM to each extract prepared as described above under (2), and the mixture was incubated at 37° C. for 30 minutes. Further, 4 times volume of a 0.2 M sodium carbonate solution was added, and the fluorescence intensity was measured at the excitation wavelength 365 nm and measurement wavelength 455 nm using an F-3010 fluorescence spectrophotometer (product of Hitachi). Separately, a regression line was prepared using 4-methylumbelliferone, and the fluorescence intensity measured was converted to the GUS activity (pmole 4-MU/min).

For luciferase activity assaying, the PicaGene emission reagent of the PicaGene emission kit PGL 100 (product of Toyo Ink Manufacturing) was added to the extract prepared as described under (2), the mixture was allowed to stand at room temperature for 30 seconds, and the emission was measured using a liquid scintillation counter (LSC-5100, product of Aloka). Separately, a regression line was prepared using the firefly luciferase enzyme solution attached to the kit, and the emission measured was converted to the luciferase enzyme amount (g), which was recorded as the luciferase activity.

The GUS activity obtained was divided by the luciferase activity for standardization. For each of the melon fruit and leaf samples, the mean value and standard deviation was calculated from three standardized GUS activity values for each fusion gene. Further, that mean value was expressed in terms of percentage relative to the mean standardized GUS activity value obtained by shooting the positive control pBI221, and the resulting percentage was reported as the relative GUS activity. The results thus obtained are shown in Table 2.

TABLE 2

| Plasmid introduced | Relative GUS activity | | |
|---|---|---|---|
| | Fruit | Mature leaf | Stem |
| pBI221 | 100 | 100 | 100 |
| p1181 | 36 | 3 | 8 |
| p310 | 42 | 1 | 3 |
| p254 | 19 | 1 | 2 |
| p234 | 39 | 1 | 4 |
| p214 | 6 | 1 | 1 |
| p89 | 5 | 1 | 1 |
| pSKGUS3C | 0 | 0 | 0 |

* Shown as relative values with the GUS activity at each site as obtained by using pBI221 being taken as 100.

EXAMPLE 6

Fruit-Specific Expression Using a Heterologous Promoter (Cauliflower Mosaic Virus (CaMV) 35S Promoter)

(1) Plasmids Used

DNA shooting into various organs by the particle gun method was carried out in the same manner as in Example 4, and the structures of the plasmids were as shown in Example 3.

(2) Extract Preparation

The immature melon fruit and mature leaf samples prepared by the method shown in Example 4 (1) were each ground in liquid nitrogen and, after thawing at room temperature, 1× PicaGene cultured cell lysing agent containing 2 mM DFP was added, followed by grinding and centrifugation. Each supernatant was used as an extract sample.

(3) GUS Activity Assay

For the cauliflower mosaic virus (CaMV) 35S promoter with the fruit-specific expression regulating DNA sequence introduced therein, the relative GUS activities in melon fruit samples were measured by the method according to Example 5. The results are shown in Table 3.

TABLE 3

| Plasmid introduced | GUS activity |
|---|---|
| pBI221 | 100 |
| pKGX | 78 |
| pX | 15 |
| p89 | 5 |

* Shown as relative values with the GUS activity obtained by using pBI221 being taken as 100.

EXAMPLE 7

Identification, by a Gel Shift Assay, of the Sequence Positively Acting on the Specific Expression and of the Sequence Negatively Acting Thereon (1) Nucleoprotein Extraction from Prince Melon An immature prince melon fruit was sliced, the seeds were removed, and the core portion alone was taken out using a knife and ice-cooled (about 320 g). Leaves were used after cutting to an appropriate size. The sample was ground in a mixer with 500 ml of ice-cooled nucleus disruption buffer (1 M hexylene glycol, 10 mM PIPES/KOH (pH 7.0), 10 mM $MgCl_2$, 5 mM 2-mercaptoethanol, 2 mM DFP, 0.2% Triton X-100) added. The resulting mixture was filtered through a 50-μm nylon mesh, and the filtrate was centrifuged at 2,000×g at 4° C. for 10 minutes. The pellet thus obtained was suspended in 80 ml of ice-cooled nucleus washing buffer (0.5 M hexylene glycol, 10 mM PIPES/KOH (pH 7.0), 10 mM $MgCl_2$, 5 mM 2-mercaptoethanol, 1 mM DFP, 0.2% Triton X-100), and a pellet was recovered by 5 minutes of centrifugation at 3,000×g at 4° C. The pellet was suspended in 20 ml of ice-cooled nucleus dissolution buffer (110 mM KCl, 15 mM Hepes/KOH (pH 7.5), 5 mM $MgCl_2$, 5 mM 2-mercaptoethanol, 1 mM DTT, 5 μg/ml antipain, 5 μg/ml leupeptin, 5 μg/ml chymostatin), and 2 ml of a 4 M ammonium sulfate solution was added dropwise to the suspension with stirring. After 30 minutes of gentle shake culture, the culture was centrifuged at 100,000×g at 4° C. for 90 minutes using a Beckman W/Ti 60 rotor. Ammonium sulfate in a fine granular form, in an amount of 0.25 g per ml of the supernatant, was added portionwise and dissolved in the supernatant. The mixture was allowed to stand overnight at 0° C. and then centrifuged at 10,000×g at 4° C. for 15 minutes. The thus-obtained pellet was suspended in 0.5 ml of ice-cooled nucleus extraction buffer (70 mM KCl, 25 mM Hepes/KOH (pH 7.5), 1 mM DTT, 0.1 mM EDTA, 10% glycerol, 5 μg/ml antipain, 5 μg/ml leupeptin, 5 μg/ml chymostatin) and dialyzed against dialysis buffer (70 mM KCl, 25 mM Hepes/KOH (pH 7.5), 1 mM mercaptoethanol, 0.1 mM EDTA, 20% glycerol) for 2 hours using the Bio-Tech dialysis cup MWCO 8000 (product of Bio-Tech), during which the buffer was exchanged four times. After dialysis, the dialyzate was centrifuged at 12,000×g at 4° C. for 10 minutes, and the supernatant obtained was divided into portions and immediately frozen in liquid nitrogen and stored at –80° C. until testing.

(2) Probes

The G probe (SEQ ID NO:7), H probe (SEQ ID NO:8), Ga probe (base sequence represented by the bases Nos. 1 to 20 in SEQ ID NO:7), Gb probe (SEQ ID NO:1) and G5 probe (base sequence represented by the bases Nos. 27 to 40 in SEQ ID NO:7) were each terminally labeled with [γ-$^{32}$P] ATP using T4 kinase.

(3) Gel Shift Assay

The binding reaction was carried out as follows. 3 μl of 5× binding buffer (200 mM KCl, 125 mM Hepes/KOH (pH 7.5), 5 mM mercaptoethanol, 0.5 mM EDTA, 50% glycerol), 2 μl of 1 μg/μl poly(dI-dC)·(dI-dC) (product of Pharmacia), 300,000 cpm of the labeled probe (prepared as described above under (2)), 3 μl of the prince melon fruit core or leaf nucleus extract of 1 μg/μl concentration (prepared as described above under (1)) were added to each well, the whole amount was made 15 μl using sterilized water, and incubation was carried out at 25° C. for 15 minutes. Each reaction mixture was electrophoresed on an undenatured 30% acrylamide gel at a constant current of 20 mA for 30 minutes, the gel was then transferred to a filter paper and dried with a gel drier. An X ray film was exposed thereto at –80° C. for 3 hours and then developed. In the case of competitive gel shift assay, the unlabeled probe, in an amount 100 times that of the labeled probe, was added as a competitive probe and the binding reaction was carried out. The results are shown in Table 4.

TABLE 4

| Probe | Fruit | Leaf |
|---|---|---|
| Probe G | 100 | 0 |
| Probe G + unlabeled probe G | 0 | 0 |
| Probe H | 5 | 0 |

\* Shown in terms of relative values with the specific band for the probe G being taken as 100.

As a result, fruit-specific strong nucleoprotein binding was observed with the G probe. Fruit-specific nucleoprotein binding was also found with the labeled Ga probe and labeled Gb probe. The GUS activity data suggest that a nucleoprotein negatively acting on the gene expression bind to the Ga probe portion and one positively acting thereon to the Gb probe moiety.

When the Gb probe labeled in the same manner was used and subjected to competition with the unlabeled G5 probe, the fruit-specific band disappeared almost completely. On the other hand, when probes derived from the G5 probe by mutation of one base were subjected to competition as unlabeled probes, the disappearance of the specific band became slight with the G5 probe-derived probe resulting from mutation of the third base T to C and the one resulting from mutation of the 7th base A to G. This indicates that the bases in those portions constitute sequences more important for the binding of the transcription factor supposedly involved in the fruit-specific expression.

INDUSTRIAL APPLICABILITY

By utilizing the DNA sequence of the invention, it has become possible to cause specific expression of a desired protein in plant fruit. As a result, the isolation and purification of a useful protein or useful substance can be facilitated by harvesting such fruit.

The invention claimed is:

1. A fruit-specific expression-regulating unit DNA sequence consisting of the DNA sequence −1181 to −1 of a cucumisin promoter that consists of the base sequence under SEQ ID NO:3 when the 3' terminus of said base sequence is numbered −1 and the 5' terminus thereof is numbered −1181.

2. A fruit-specific expression-regulating unit DNA sequence consisting of the DNA sequence −865 to −1 of a cucumisin promoter that consists of the base sequence under SEQ ID NO:3 when the 3' terminus of said base sequence is numbered −1 and the 5' terminus thereof is numbered −1181.

3. A fruit-specific expression-regulating unit DNA sequence consisting of the DNA sequence −371 to −1 of a cucumisin promoter that consists of the base sequence under SEQ ID NO:3 when the 3' terminus of said base sequence is numbered −1 and the 5' terminus thereof is numbered −1181.

4. A fruit-specific expression-regulating unit DNA sequence consisting of the DNA sequence −310 to −1 of a cucumisin promoter that consists of the base sequence under SEQ ID NO:3 when the 3' terminus of said base sequence is numbered −1 and the 5' terminus thereof is numbered −1181.

5. A fruit-specific expression-regulating unit DNA sequence consisting of the DNA sequence −254 to −1 of a cucumisin promoter that consists of the base sequence under SEQ ID NO:3 when the 3' terminus of said base sequence is numbered −1 and the 5' terminus thereof is numbered −1181.

6. A fruit-specific expression-regulating unit DNA sequence consisting of the DNA sequence −234 to −1 of a cucumisin promoter that consists of the base sequence under SEQ ID NO:3 when the 3' terminus of said base sequence is numbered −1 and the 5' terminus thereof is numbered −1181.

7. A plasmid which comprises a DNA coding for a structural gene product that is expressed in a plant or for a corresponding antisense RNA, a terminator for said DNA, which terminator functions in the plant, and the DNA sequence according to claim 1 for regulating specific expression of said DNA in said plant.

8. A plasmid which comprises a DNA coding for a structural gene product that is expressed in a plant or for a corresponding antisense RNA, a terminator for said DNA, which terminator functions in the plant, and the DNA sequence according to claim 2 for regulating specific expression of said DNA in said plant.

9. A plasmid which comprises a DNA coding for a structural gene product that is expressed in a plant or for a corresponding antisense RNA, a terminator for said DNA, which terminator functions in the plant, and the DNA sequence according to claim 3 for regulating specific expression of said DNA in said plant.

10. A plasmid which comprises a DNA coding for a structural gene product that is expressed in a plant or for a corresponding antisense RNA, a terminator for said DNA, which terminator functions in the plant, and the DNA sequence according to claim 4 for regulating specific expression of said DNA in said plant.

11. A plasmid which comprises a DNA coding for a structural gene product that is expressed in a plant or for a corresponding antisense RNA, a terminator for said DNA, which terminator functions in the plant, and the DNA sequence according to claim 5 for regulating specific expression of said DNA in said plant.

12. A plasmid which comprises a DNA coding for a structural gene product that is expressed in a plant or for a corresponding antisense RNA, a terminator for said DNA, which terminator functions in the plant, and the DNA sequence according to claim 6 for regulating specific expression of said DNA in said plant.

13. A plant cell which is transformed with the plasmid according to claim 7.

14. A plant cell which is transformed with the plasmid according to claim 8.

15. A plant cell which is transformed with the plasmid according to claim 9.

16. A plant cell which is transformed with the plasmid according to claim 10.

17. A plant cell which is transformed with the plasmid according to claim 11.

18. A plant cell which is transformed with the plasmid according to claim 12.

19. A plant body which is transformed with the plasmid according to claim 7.

20. A plant body which is transformed with the plasmid according to claim 8.

21. A plant body which is transformed with the plasmid according to claim 9.

22. A plant body which is transformed with the plasmid according to claim 10.

23. A plant body which is transformed with the plasmid according to claim 11.

24. A plant body which is transformed with the plasmid according to claim 12.

25. A microorganism harboring the plasmid according to claim 7.

26. A microorganism harboring the plasmid according to claim 8.

27. A microorganism harboring the plasmid according to claim 9.

28. A microorganism harboring the plasmid according to claim 10.

29. A microorganism harboring the plasmid according to claim 11.

30. A microorganism harboring the plasmid according to claim 12.

* * * * *